United States Patent
Kang et al.

(10) Patent No.: US 11,462,100 B2
(45) Date of Patent: Oct. 4, 2022

(54) TRAFFIC SURVEILLANCE SYSTEM USING ERROR MONITORING

(71) Applicants: HYUNDAI MOTOR COMPANY, Seoul (KR); KIA MOTORS CORPORATION, Seoul (KR); Sookmyung Women's University Industry-Academic Cooperation Foundation, Seoul (KR)

(72) Inventors: Jeong Su Kang, Seongnam-si (KR); Suh Yeon Dong, Seoul (KR)

(73) Assignees: Hyundai Motor Company, Seoul (KR); Kia Motors Corporation, Seoul (KR); Sookmyung Women's University Industry-Academic Cooperation Foundation, Seoul (KR)

( * ) Notice: Subject to any disclaimer, the term of this patent is extended or adjusted under 35 U.S.C. 154(b) by 216 days.

(21) Appl. No.: 16/923,821

(22) Filed: Jul. 8, 2020

(65) Prior Publication Data
US 2021/0012650 A1   Jan. 14, 2021

(30) Foreign Application Priority Data
Jul. 11, 2019   (KR) ........................ 10-2019-0083758

(51) Int. Cl.
*G08G 1/01*   (2006.01)
*A61B 5/16*   (2006.01)
(Continued)

(52) U.S. Cl.
CPC ......... *G08G 1/0137* (2013.01); *A61B 5/0006* (2013.01); *A61B 5/165* (2013.01); *A61B 5/369* (2021.01); *A61B 2503/12* (2013.01)

(58) Field of Classification Search
CPC .... G08G 1/0137; A61B 5/369; A61B 5/0006; A61B 5/165; A61B 2503/12
See application file for complete search history.

(56) References Cited

U.S. PATENT DOCUMENTS

| 6,115,631 A * | 9/2000 | Heyrend | ............... | A61B 5/377 |
| | | | | 600/544 |
| 10,960,225 B2 * | 3/2021 | Adaikkan | ............ | A61N 5/1001 |

(Continued)

OTHER PUBLICATIONS

Hilmani et al., Automated Real-Time Intelligent Traffic Control System for Smart Cities Using Wireless Sensor Networks (Year: 2020).*

(Continued)

*Primary Examiner* — Quang Pham
(74) *Attorney, Agent, or Firm* — Fox Rothschild LLP

(57) ABSTRACT

An error monitoring apparatus and method are provided. The error monitoring method includes collecting an Event-Related Potential (ERP) for at least one passenger in a first mobility for a predetermined amount of time, analyzing the ERP collected for the predetermined amount of time, and transmitting error information of the first mobility to a traffic control server based on a result of analysis. The error information of the first mobility includes at least one of information on a time when the ERP is generated, a waveform of the ERP, position information of the first mobility or operation information of a second mobility, and the second mobility is different from the first mobility and has caused the ERP.

19 Claims, 13 Drawing Sheets

(51) Int. Cl.
*A61B 5/00* (2006.01)
*A61B 5/369* (2021.01)

(56) References Cited

U.S. PATENT DOCUMENTS

| | | | | |
|---|---|---|---|---|
| 2007/0027579 A1* | 2/2007 | Suzuki | G05D 1/12 | 700/245 |
| 2007/0250334 A1* | 10/2007 | Reeves | G08G 1/0104 | 340/933 |
| 2009/0023422 A1* | 1/2009 | MacInnis | A61B 5/1112 | 455/411 |
| 2009/0023428 A1* | 1/2009 | Behzad | H04W 4/02 | 455/414.3 |
| 2009/0309974 A1* | 12/2009 | Agrawal | G08G 1/054 | 709/201 |
| 2010/0284382 A1* | 11/2010 | Stahlin | G08G 1/095 | 370/338 |
| 2011/0279676 A1* | 11/2011 | Terada | G08B 21/02 | 348/148 |
| 2012/0288108 A1* | 11/2012 | Adachi | A61B 5/38 | 381/60 |
| 2013/0039498 A1* | 2/2013 | Adachi | A61B 5/12 | 704/E11.001 |
| 2013/0053720 A1* | 2/2013 | Sakaguchi | A61B 5/377 | 600/544 |
| 2013/0070929 A1* | 3/2013 | Adachi | H04R 29/001 | 381/56 |
| 2013/0131535 A1* | 5/2013 | Sun | A61B 5/378 | 600/544 |
| 2013/0138012 A1* | 5/2013 | Morikawa | A61B 5/38 | 600/545 |
| 2013/0179087 A1* | 7/2013 | Garripoli | A61B 5/374 | 702/19 |
| 2013/0184552 A1* | 7/2013 | Westermann | A61B 5/38 | 600/378 |
| 2013/0266163 A1* | 10/2013 | Morikawa | A61B 5/6803 | 381/312 |
| 2013/0296732 A1* | 11/2013 | Adachi | A61B 5/378 | 600/544 |
| 2013/0324880 A1* | 12/2013 | Adachi | A61B 5/38 | 600/545 |
| 2013/0338527 A1* | 12/2013 | Suh | A61B 5/316 | 600/544 |
| 2014/0072127 A1* | 3/2014 | Adachi | A61B 5/125 | 381/56 |
| 2014/0072130 A1* | 3/2014 | Adachi | H04R 25/30 | 381/60 |
| 2014/0105436 A1* | 4/2014 | Adachi | A61B 5/38 | 381/321 |
| 2014/0135644 A1* | 5/2014 | Kim | A61B 5/0024 | 600/545 |
| 2014/0153729 A1* | 6/2014 | Adachi | A61B 5/38 | 381/60 |
| 2015/0297109 A1* | 10/2015 | Garten | A61B 5/316 | 600/28 |
| 2015/0317523 A1* | 11/2015 | Clark | G08B 21/02 | 348/148 |
| 2015/0350794 A1* | 12/2015 | Pontoppidan | A61B 5/125 | 381/321 |
| 2016/0275798 A1* | 9/2016 | Maytal | G08B 21/187 | |
| 2017/0080256 A1* | 3/2017 | Kim | A61B 5/4836 | |
| 2017/0330475 A1* | 11/2017 | Minoda | G09B 7/06 | |
| 2018/0061237 A1* | 3/2018 | Erickson | G08G 1/0112 | |
| 2018/0170354 A1* | 6/2018 | Lee | B60W 30/182 | |
| 2019/0005412 A1* | 1/2019 | Matus | G06Q 30/0201 | |
| 2019/0082044 A1* | 3/2019 | Melendez | H04W 4/023 | |
| 2019/0122543 A1* | 4/2019 | Matus | G08G 1/0141 | |
| 2019/0130663 A1* | 5/2019 | Li | G06V 20/59 | |
| 2019/0132733 A1* | 5/2019 | Castinado | G16H 30/40 | |
| 2019/0180602 A1* | 6/2019 | Han | H04W 4/025 | |
| 2019/0223747 A1* | 7/2019 | Chou | A61B 5/4812 | |
| 2019/0290217 A1* | 9/2019 | Long | A61B 5/746 | |
| 2019/0348041 A1* | 11/2019 | Cella | G10L 15/16 | |
| 2019/0387998 A1* | 12/2019 | Garten | A61M 21/00 | |
| 2020/0012346 A1* | 1/2020 | Schiff | A61B 5/168 | |
| 2020/0043326 A1* | 2/2020 | Tao | B60R 11/04 | |
| 2020/0261689 A1* | 8/2020 | Harrison | A61B 5/7264 | |
| 2021/0011545 A1* | 1/2021 | Min | G06F 3/011 | |
| 2021/0208282 A1* | 7/2021 | Hamaguchi | G08G 1/0133 | |

OTHER PUBLICATIONS

Hussain et al., Driving-Induced Neurological Biomarkers in an Advanced Driver-Assistance System (Year: 2021).*

Abreha et al., Federated Learning in Edge Computing a Systematic Survey (Year: 2020).*

* cited by examiner

FIG. 4A
FIG. 4B
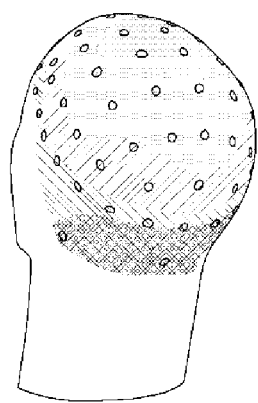
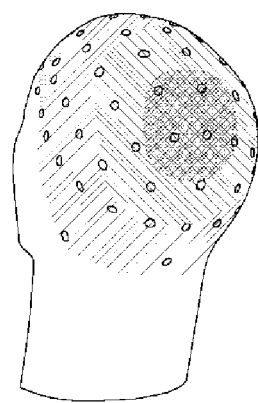
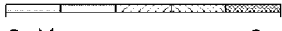
−9.3μV    −0.6μV
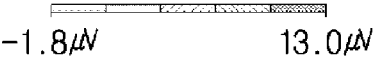
−1.8μV    13.0μV

TRAFFIC SURVEILLANCE SYSTEM USING ERROR MONITORING

CROSS-REFERENCE TO RELATED APPLICATION

The present application claims priority to and the benefit of Korean Patent Application No. 10-2019-0083758, filed Jul. 11, 2019, which is incorporated herein for all purposes by this reference in its entirety.

TECHNICAL FIELD

The present disclosure relates to a mobility controlling method and apparatus. More particularly, the present disclosure relates to a mobility controlling method and apparatus based on error monitoring.

BACKGROUND

The statements in this section merely provide background information related to the present disclosure and may not constitute prior art.

As one of the transport means, a vehicle (or mobility) is a very important means and tool for living a life in the modern world. Furthermore, a vehicle itself may be regarded as something special that gives meaning to someone.

As technology is advanced, functions provided by a vehicle also gradually evolve. For example, in recent years, vehicles not only transport a passenger to a destination, but also meet a passenger's needs for faster and safer travel to a destination. In addition, new devices are being added to a vehicle system in order to satisfy a passenger's aesthetic taste and comfort. In addition, the existing devices like steering wheels, transmissions and acceleration/deceleration devices are also being developed so that more functions can be provided to users.

Meanwhile, a brain-computer interface or a brain-machine interface is a field of controlling a computer or a machine according to a person's intention by using brain wave signals. ERP (Event-Related Potential) is closely related to cognitive functions.

SUMMARY the present disclosure provides a traffic surveillance system.

The present disclosure provides a traffic surveillance system for determining whether to follow traffic rules based on error monitoring.

The present disclosure provides an error monitoring apparatus for performing error monitoring.

The present disclosure provides a traffic control server for determining whether to follow traffic rules of a mobility based on error monitoring.

According to the present disclosure, an error monitoring apparatus includes a sensing unit configured to collect an Event-Related Potential (ERP) for at least one passenger in a first mobility for a predetermined time, an analysis unit configured to analyze the ERP collected for the predetermined time, and a transmission unit configured to transmit error information of the first mobility to a traffic control server based on a result of analysis. The error information of the first mobility includes at least one of information on a time when the ERP is generated, a waveform of the ERP, position information of the first mobility and operation information of a second mobility, and the second mobility is different from the first mobility and has caused the ERP.

In some forms of the present disclosure, the ERP may include at least one of Error-Related Negativity (ERN) and Error Positivity (Pe).

In some forms of the present disclosure, the ERP may include at least one of Correct-Related Negativity (CRN) and Correct Positivity (Pc).

In some forms of the present disclosure, the analysis may include comparing an amplitude of the ERP collected for the predetermined time with a predetermined threshold.

In some forms of the present disclosure, the predetermined threshold may be differently determined according to at least one of a type of the ERP and a passenger, from which the ERP is obtained.

In some forms of the present disclosure, the transmission unit may transmit the error information of the first mobility to the traffic control server, when the amplitude of the ERP collected for the predetermined time is out of a predetermined threshold range.

In some forms of the present disclosure, the sensing unit may measure a brain wave signal of at least one passenger in the first mobility and detect the ERP from the measured brain wave signal, and the ERP may include a response-locked ERP.

In some forms of the present disclosure, the analysis may include determining whether an amplitude of the ERP is in a predetermined threshold value during a predetermined time interval.

In some forms of the present disclosure, the analysis may be performed using a brain wave signal template of the at least one passenger, and the brain wave signal may be a brain wave signal in a time domain, which is previously obtained within a predetermined time range after generation of the ERP.

In addition, in some forms of the present disclosure, a traffic control server includes a reception unit configured to receive error information of a first mobility from the first mobility, and a controller configured to determine a second mobility based on the error information of the first mobility. The error information of the first mobility includes at least one of information on a time when the ERP is generated, a waveform of the ERP, position information of the first mobility and operation information of a second mobility, and the second mobility is different from the first mobility and has caused the ERP.

In some forms of the present disclosure, the controller may further determine whether the second mobility has violated predetermined traffic rules.

In some forms of the present disclosure, the controller may impose, on the second mobility, at least one of a fine, a penalty or a forfeit corresponding to violation of the predetermined traffic rules, upon determining that the second mobility has violated the predetermined traffic rules.

In some forms of the present disclosure, the reception unit may further receive error information of a third mobility from the third mobility, the controller may determine the second mobility based on the error information of the first mobility and the error information of the third mobility, and the third mobility may be different from the first mobility and the second mobility and may be located in a predetermined range from the first mobility.

In addition, in some forms of the present disclosure, a traffic surveillance system includes an error monitoring apparatus configured to transmit error information of a mobility to a server, and a traffic control server configured to determine a traffic rule violation mobility using the error information of the mobility. The error monitoring server collects an Event-Related Potential (ERP) for at least one passenger in a first mobility for a predetermined time, analyzes the ERP collected for the predetermined time, and transmits error information of the first mobility to the traffic control server based on a result of analysis, the traffic control server receives the error information of the first mobility from the error monitoring apparatus and determines a second mobility based on the error information of the first mobility, the error information of the first mobility includes at least one of information on a time when the ERP is generated, a waveform of the ERP, position information of the first mobility and operation information of a second mobility, and the second mobility is different from the first mobility and has caused the ERP.

In addition, in some forms of the present disclosure, an error monitoring method includes collecting an Event-Related Potential (ERP) for at least one passenger in a first mobility for a predetermined time, analyzing the ERP collected for the predetermined time, and transmitting error information of the first mobility to a traffic control server based on a result of analysis. The error information of the first mobility includes at least one of information on a time when the ERP is generated, a waveform of the ERP, position information of the first mobility and operation information of a second mobility, and the second mobility is different from the first mobility and has caused the ERP.

In some forms of the present disclosure, the ERP may include at least one of Error-Related Negativity (ERN) and Error Positivity (Pe).

In some forms of the present disclosure, the ERP may include at least one of Correct-Related Negativity (CRN) and Correct Positivity (Pc).

In some forms of the present disclosure, the analysis may include comparing an amplitude of the ERP collected for the predetermined time with a predetermined threshold.

In some forms of the present disclosure, the predetermined threshold may be differently determined according to at least one of a type of the ERP and a passenger, from which the ERP is obtained.

In some forms of the present disclosure, the transmitting of the error information of the first mobility to the traffic control server may include transmitting the error information of the first mobility to the traffic control server, when the amplitude of the ERP collected for the predetermined time is out of a predetermined threshold range.

In some forms of the present disclosure, the collecting of the ERP for the at least one passenger in the first mobility may include measuring a brain wave signal of at least one passenger in the first mobility and detecting the ERP from the measured brain wave signal, and the ERP may include a response-locked ERP.

In some forms of the present disclosure, the analysis may include determining whether an amplitude of the ERP is in a predetermined threshold range for a predetermined time interval.

In some forms of the present disclosure, the analysis may be performed using a brain wave signal template of the at least one passenger, and the brain wave signal may be a brain wave signal in a time domain, which is previously obtained within a predetermined time range after generation of the ERP.

In addition, in some forms of the present disclosure, a method of operating a traffic control server includes receiving error information of a first mobility from the first mobility, determining a second mobility based on the error information of the first mobility. The error information of the first mobility includes at least one of information on a time when the ERP is generated, a waveform of the ERP, position information of the first mobility and operation information of a second mobility, and the second mobility is different from the first mobility and has caused the ERP.

In some forms of the present disclosure, the method may further include determining whether the second mobility has violated predetermined traffic rules.

In some forms of the present disclosure, the method may further include imposing, on the second mobility, at least one of a fine, a penalty or a forfeit corresponding to violation of the predetermined traffic rules, upon determining that the second mobility has violated the predetermined traffic rules.

In some forms of the present disclosure, the method may further include receiving error information of a third mobility from the third mobility and determining the second mobility based on the error information of the first mobility and the error information of the third mobility, and the third mobility may be different from the first mobility and the second mobility and may be located in a predetermined range from the first mobility.

The features briefly summarized above with respect to the present disclosure are merely exemplary aspects of the detailed description below of the present disclosure, and do not limit the scope of the present disclosure.

DRAWINGS

In order that the disclosure may be well understood, there will now be described various forms thereof, given by way of example, reference being made to the accompanying drawings, in which:

FIGS. 4A and 4B are views respectively illustrating measurement areas of ERP and Pe in one form of the present disclosure;

Figure 1:
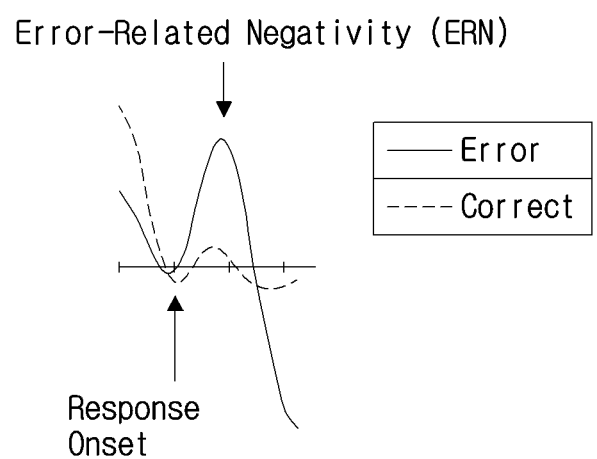
FIG. 1 is a view illustrating a general waveform of ERN in one form of the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Exemplary forms of the present disclosure will be described in detail such that the ordinarily skilled in the art would easily understand and implement an apparatus and a method provided by the present disclosure in conjunction with the accompanying drawings. However, the present disclosure may be embodied in various forms and the scope of the present disclosure should not be construed as being limited to the exemplary forms.

In describing forms of the present disclosure, well-known functions or constructions will not be described in detail when they may obscure the spirit of the present disclosure.

In the present disclosure, it will be understood that when an element is referred to as being "connected to", "coupled to", or "combined with" another element, it can be directly connected or coupled to or combined with the another element or intervening elements may be present therebetween. It will be further understood that the terms "comprises", "includes", "have", etc. when used in the present disclosure specify the presence of stated features, integers, steps, operations, elements, components, and/or combinations thereof but do not preclude the presence or addition of one or more other features, integers, steps, operations, elements, components, and/or combinations thereof.

It will be understood that, although the terms "first", "second", etc. may be used herein to describe various elements, these elements should not be limited by these terms. These terms are only used to distinguish one element from another element and not used to show order or priority among elements. For instance, a first element discussed below could be termed a second element without departing from the teachings of the present disclosure. Similarly, the second element could also be termed as the first element.

In the present disclosure, distinguished elements are termed to clearly describe features of various elements and do not mean that the elements are physically separated from each other. That is, a plurality of distinguished elements may be combined into a single hardware unit or a single software unit, and conversely one element may be implemented by a plurality of hardware units or software units. Accordingly, although not specifically stated, an integrated form of various elements or separated forms of one element may fall within the scope of the present disclosure. Also, the terms, such as 'unit' or 'module', etc., should be understood as a unit that processes at least one function or operation and that may be embodied in a hardware manner (e.g., a processor), a software manner, or a combination of the hardware manner and the software manner.

In the present disclosure, all of the constituent elements described in various forms should not be construed as being essential elements but some of the constituent elements may be optional elements. Accordingly, forms configured by respective subsets of constituent elements in a certain form also may fall within the scope of the present disclosure. In addition, forms configured by adding one or more elements to various elements also may fall within the scope of the present disclosure.

As an electrical activity of neurons constituting a brain, a brain wave signal (or brain signal, brain wave) means a bio signal that directly and indirectly reflects a conscious or nonconscious state of a person. A brain wave signal can be measured in every area of human scalp, and its wavelength has a frequency of mainly 30 Hz or below and a potential difference of scores of microvolts. Depending on brain activity and state, various waveforms may appear. A research on interface control using a brain wave signal according to a person's intention is under way. A brain wave signal may be obtained by using EEG (Electro Encephalo Graphy) using electrical signals caused by brain activities, MEG (Magneto Encephalo Graphy) using magnetic signals occurring with electrical signals, and fMRI (functional Magnetic Resonance Imaging) or fNIRS (Near-Infrared Spectroscopy) using a change of oxygen saturation in the blood. Although fMRI and fNIRS are useful techniques for measuring brain activities, fMRI has a low time-resolution and fNIRS has a low spatial-resolution in general. Due to these limitations, EEG signals are mostly used by virtue of excellent portability and time-resolution.

A brain wave signal changes spatially and over time according to brain activity. As a brain wave signal is usually difficult to analyze and its waveform is not easy to visually analyze, various processing methods are proposed.

For example, according to the number of oscillations (frequency), brain wave signals may be classified based on frequency bands (Power spectrum classification). The classification considers a measured brain wave signal as a linear sum of simple signals at each specific frequency, decomposes the signal into each frequency component and indicates a corresponding amplitude. A brain wave signal at each frequency may be obtained by using pre-processing normally for noise elimination, the Fourier transform into frequency domain, and a band-pass filter (BPF).

More particularly, according to frequency band, brain waves may be classified into delta, theta, alpha, beta and gamma waves. Delta waves are brain waves with a frequency of 3.5 Hz or below and an amplitude of 20~200 μV, mainly appearing in normal deep sleep or newborns. In addition, delta waves may increase as our awareness of the physical world decreases. Generally, theta waves are brain waves with a frequency of 3.5~7 Hz, mainly appearing in emotionally stable states or in sleep.

In addition, theta waves are generated mainly in the parietal cortex and in the occipital cortex and may appear during calm concentration for recollecting a memory or meditating. Generally, alpha waves are brain waves with a frequency of 8~12 Hz, mainly appearing in relaxed and comfortable states. In addition, alpha waves are normally generated in the occipital cortex during rest and may diminish in sleep. Generally, beta waves are brain waves with a frequency of 13~30 Hz, mainly appearing in a state of tension, which is bearable enough, or while a certain level of attention is paid. In addition, beta waves are mainly generated in the frontal cortex and are related to an awakened state or concentrated brain activities, pathological phenomena and medicinal effects. Beta waves may appear in a wide area throughout the brain. In addition, specifically, the beta waves may be divided into SMR waves with a frequency of 13~15 Hz, mid-beta waves with a frequency of 15~18 Hz and high beta waves with a frequency of 20 Hz and above. As beta waves appear to be stronger under stress like anxiety and tension, they are called stress waves. Gamma waves are brain waves that generally have a frequency of 30~50 Hz, mainly appearing in a strongly excited state or during high-level cognitive information processing. In addition, gamma waves may appear in an awaking state of consciousness and during REM sleep and may also be overlapped with beta waves.

Each of the brain wave signals according to frequency band is associated with a specific cognitive function. For example, delta waves are associated with sleep, theta waves are associated with working memory, and alpha waves are associated with attention or inhibition. Thus, the property of a brain wave signal at each frequency band selectively displays a specific cognitive function. In addition, the brain wave signal at each frequency band may show a little different aspect in each measuring part on the surface of head. The cerebral cortex may be divided into frontal cortex, parietal cortex, temporal cortex and occipital cortex. These parts may have a few different roles. For example, the occipital cortex corresponding to the back of head has the primary visual cortex and thus can primarily process visual information. The parietal cortex located near the top of head has the somatosensory cortex and thus can process motor/sensory information. In addition, the frontal cortex can process information related to memory and thinking, and the temporal cortex can process information related to auditory sense and olfactory sense.

Meanwhile, for another example, a brain wave signal may be analyzed by using ERP (Event-Related Potential). ERP is an electrical change in a brain in association with a stimulus from outside or a psychological process inside. ERP means a signal including an electrical activity of the brain, which is caused by a stimulus including specific information (for example, image, voice, sound, command of execution, etc.) after a certain time since the stimulus is presented.

To analyze an ERP, a process of separating a signal from a noise is desired. An averaging method may be mainly used. Particularly, by averaging brain waves measured based on stimulus onset time, it is possible to remove brain waves, which are not related to a stimulus, and to pick out only a related potential, that is, a brain activity commonly associated with stimulus processing.

As ERP has a high time resolution, it is closely related to a research on cognitive function. ERP is an electrical phenomenon that is evoked by an external stimulus or is related to an internal state. According to types of stimuli, ERPs may be classified into auditory sense-related potentials, sight-related potentials, somatic sense-related potentials and olfactory sense-related potentials. According to properties of stimuli, ERPs may be classified into exogenous ERPs and endogenous ERPs. Exogenous ERPs have a waveform determined by an external stimulus, are related to automatic processing, and mainly appear in the initial phase of being given the stimulus. For example, exogenous ERPs are brainstem potentials. On the other hand, endogenous ERPs are determined by an internal cognitive process or a psychological process or state, irrespective of stimuli, and are related to 'controlled processing'. For example, endogenous ERPs are P300, N400, P600, CNV (Contingent Negative Variation), etc.

Names given to ERP peaks normally include a polarity and a latent period, and the peak of each signal has an individual definition and meaning. For example, the positive potential is P, the negative potential is N, and P300 means a positive peak measured about 300 ms after the onset of a stimulus. In addition, 1, 2, 3 or a, b, c and the like are applied according to the order of appearance. For example, P3 means a third positive potential in waveform after the onset of a stimulus.

Hereinafter, various ERPs will be described.

For example, N100 is related to a response to an unpredictable stimulus.

MMN (Mismatch Negativity) may be generated not only by a focused stimulus but also by non-focused stimulus. MMN may be used as an indicator for whether or not a sense memory (echoic memory) operates before initial attention. P300, which will be described below, appears in a process of paying attention and making judgment, while MMN is analyzed as a process occurring in the brain before paying attention.

For another example, N200 (or N2) is mainly generated according to visual and auditory stimuli and is related to short-term memory or long-term memory, which are types of memories after attention, along with P300 described below.

For yet another example, P300 (or P3) mainly reflects attention to a stimulus, stimulus cognition, memory search and alleviation of uncertain feeling and is related to perceptual decision distinguishing stimuli from outside. As the generation of P300 is related to a cognitive function, P300 is generated irrespective of types of presented stimuli. For example, P300 may be generated in auditory stimuli, visual stimuli and somatic stimuli. P300 is widely applied to a research on brain-computer interface.

For yet another example, N400 is related to language processing and is caused when a sentence or an auditory stimulus with a semantic error is presented. In addition, N400 is related to a memory process and may reflect a process of retrieving or searching information from long-term memory.

For yet another example, as an indicator showing reconstruction or recollective process, P600 is related to a process of processing a stimulus more accurately based on information stored in long-term memory.

For yet another example, CNV refers to potentials appearing for 200~300 ms and even for a few seconds in the later phase. It is also called slow potentials (SPs) and is related to expectancy, preparation, mental priming, association, attention and motor activity.

For yet another example, ERN (Error-Related Negativity) or Ne (error negativity) is an event-related potential (ERP) generated by a mistake or an error. It may occur when a subject makes a mistake in a sensorimotor task or a similar task. More particularly, when a subject cognizes a mistake or an error, ERN is generated and its negative peak appears mainly in the frontal and central zones for about 50~150 ms. Especially, it may appear in a situation, where a mistake related to motor response is likely to occur, and may also be used to indicate a negative self-judgment.

Hereinafter, the major features of ERN will be described in more detail.

FIG. 1 is a view illustrating a general waveform of ERN according to one form of the present disclosure.

Referring to FIG. 1, negative potential values are depicted above the horizontal axis, and positive potential values are depicted below the horizontal axis. In addition, it can be confirmed that an ERP with a negative peak value is generated within a predetermined time range after a response onset for an arbitrary motion. Herein, the response may mean a case where a mistake or an error is made (Error Response). In addition, the predetermined time range may be about 50 ~150 ms. Alternatively, the predetermined time range may be about 0 ~100 ms. Meanwhile, in the case of a correct response, an ERP is generated which has a relatively smaller negative peak than ERN.

As an ERP of initial negativity, ERN is time-locked until a response error occurs. In addition, ERN is known to reflect the reinforcement activity of a dopaminergic system related to behavioral monitoring. ERN includes the fronto-striatal loop including the rostral cingulate zone. Meanwhile, dopamine is associated with the reward system of brain that usually forms a specific behavior and motivates a person thereby providing pleasure and reinforced feelings. When a behavior obtaining an appropriate reward is repeated, it is learned as a habit. In addition, more dopamine is released through emotional learning, and a new behavior is attempted due to the release of dopamine. Thus, reward-driven learning is called reinforcement learning.

In addition, ERN may be generated in 0 ~100 ms after the onset of an erroneous response that is caused during an interference task (for example, Go-noGo task, Stroop task, Flanker task, and Simon task) through the frontal cortex lead.

In addition, together with CRN described below, ERN is known to reflect a general behavior monitoring system that can distinguish a right behavior and a wrong behavior.

In addition, the fact that ERN reaches a maximum amplitude at the frontal cortex electrode is known to reflect that an intracerebral generator is located in the rostral cingulate zone or the dorsal anterior cingulate cortex (dACC) zone.

In addition, ERN may show a change of amplitude according to a negative emotional state.

In addition, ERN may be reported even in a situation where behavioral monitoring is performed based on external evaluation feedback processing unlike internal motor expression, and may be classified as FRN described below.

In addition, ERN may be generated not only when having cognized a mistake or an error but also before cognizing the mistake or the error.

In addition, ERN may be generated not only as a response to his/her own mistake or error but also as a response to a mistake or error of others.

In addition, ERN may be generated not only as a response to a mistake or an error but also as a response to anxiety or stress for a predetermined performance task or object.

Meanwhile, for yet another example, being an event-related potential (ERP) that is generated after ERN, Pe (Error Positivity) is an ERP with a positive value, which is generated mainly at the frontal cortex electrode in about 150 ~300 ms after a mistake or an error. Pe is known as a reaction that realizes a mistake or an error and pays more attention. In other words, Pe is related to an indicator of a conscious error information processing process after error detection. ERN and Pe are known as ERPs related to error monitoring.

Hereinafter, the major features of Pe will be described in more detail.

Figure 2:
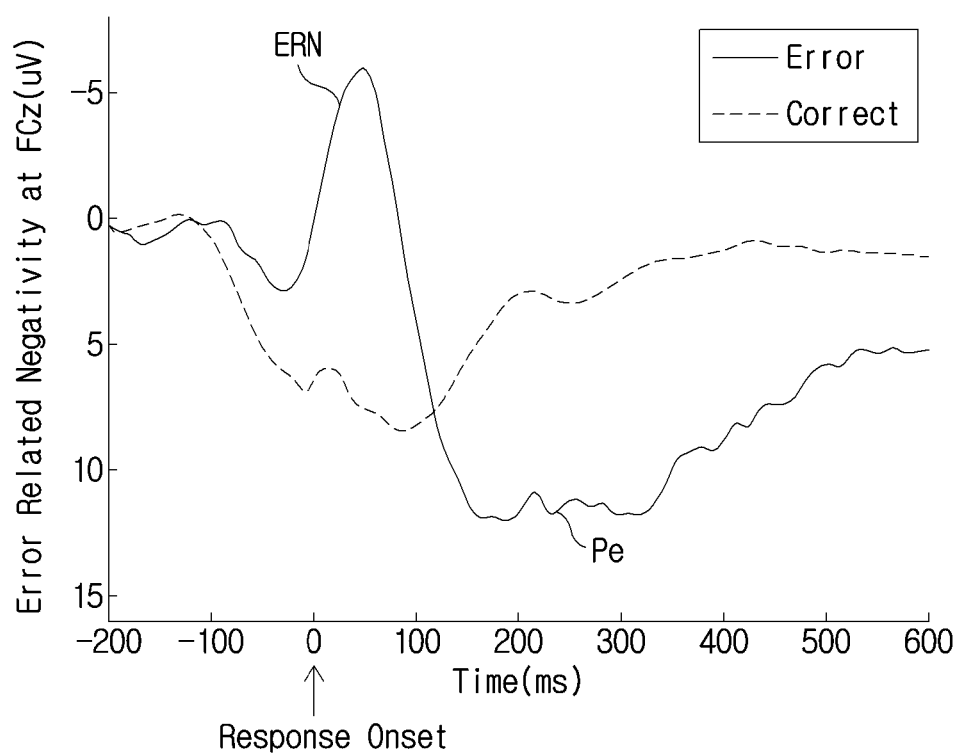
FIG. 2 is a view illustrating general waveforms of ERN and Pe according to one form of the present disclosure.

FIG. 2 is a view illustrating general waveforms of ERN and Pe according to another form of the present disclosure.

Referring to FIG. 2, negative potential values are depicted above positive potential values. In addition, it can be confirmed that an ERP with a negative peak value, that is, an ERN is generated within a first predetermined time range after a response onset for an arbitrary motion. Herein, the response may mean a case where a mistake or an error is made (Error Response). In addition, the first predetermined time range may be about 50 ~150 ms. Alternatively, the first predetermined time range may be about 0 ~200 ms.

In addition, it can be confirmed that an ERP with a positive peak value, that is, a Pe is generated within a second predetermined time range after the onset of the ERN. In addition, the second predetermined time range may be about 150 ~300 ms after an error onset. Alternatively, the second predetermined time range may mean about 200~400 ms.

Figure 3:
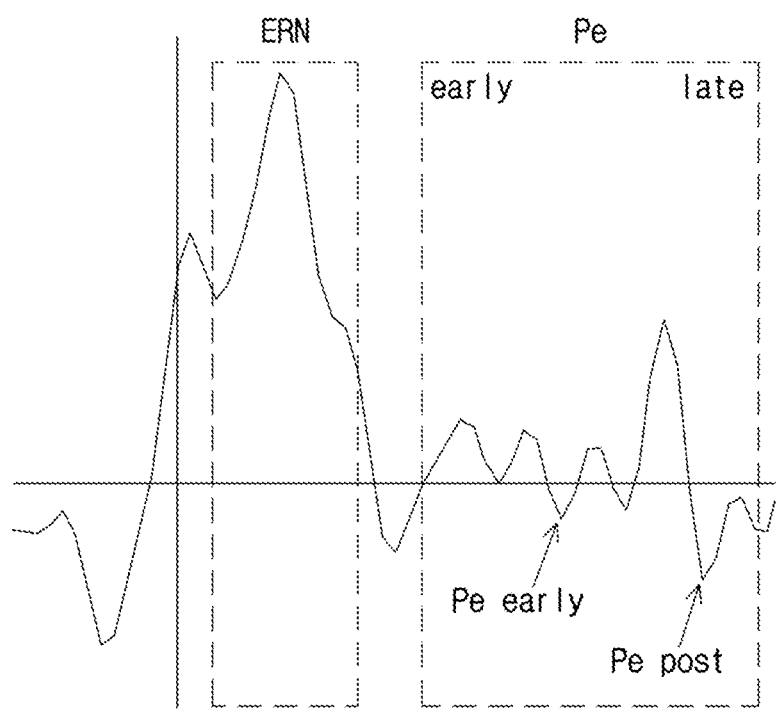
FIG. 3 is a view illustrating a deflection characteristic of Pe according to another form of the present disclosure.

FIG. 3 is a view illustrating a deflection characteristic of Pe in one form of the present disclosure.

Referring to FIG. 3, like P3, Pe has a wide deflection characteristic, and the plexus generator includes not only the areas of posterior cingulate cortex and insula cortex but also more anterior cingulate cortex.

In addition, Pe may reflect an emotional evaluation of an error and an attention to a stimulus like P300. In addition, ERN indicates a conflict between a right response and a wrong response, and Pe is known to be a response that realizes a mistake and pays more attention. In other words, ERN may be generated in a process of detecting a stimulus, and Pe may be generated depending on attention in a process of processing a stimulus. When ERN and/or Pe have relatively large values respectively, it is known that the values are related to an adaptive behavior intended to respond more slowly and more accurately after a mistake.

FIGS. 4A and 4B are views illustrating measurement areas of ERP and Pe according to one form of the present disclosure.

ERN and Pe are known as ERPs related to error monitoring. Regarding the measurement areas of ERN and Pe, a largest negative value and a largest positive value may normally be measured in the central area. However, there may be a little difference according to measurement conditions. For example, FIG. 4A is the main area where ERN is measured, and the largest negative value of ERN may normally be measured in the midline frontal or central zone (that is, FCZ). In addition, FIG. 4B is the main area where Pe is measured, and a large positive value of Pe may normally be measured in a posterior midline zone as compared to ERN.

Meanwhile, for yet another example, FRN (Feedback-Related Negativity) is an event-related potential (ERP) that is related to error detection obtained based on external evaluation feedback. ERN and/or Pe detect an error based on an internal monitoring process. However, in the case of FRN, when being obtained based on external evaluation feedback, it may operate similarly to the process of ERN.

In addition, FRN and ERN may share many electrophysiological properties. For example, FRN has a negative peak value at the frontal cortex electrode in about 250~300 ms after the onset of a negative feedback and may be generated in the dorsal anterior cingulate cortex (dACC) zone like ERN.

In addition, like ERN, FRN may reflect an activity of reinforcement learning by a dopaminergic system. In addition, FRN normally has a larger negative value than a positive feedback and may have a larger value for an unforeseen case than for a predictable result.

Figure 5:
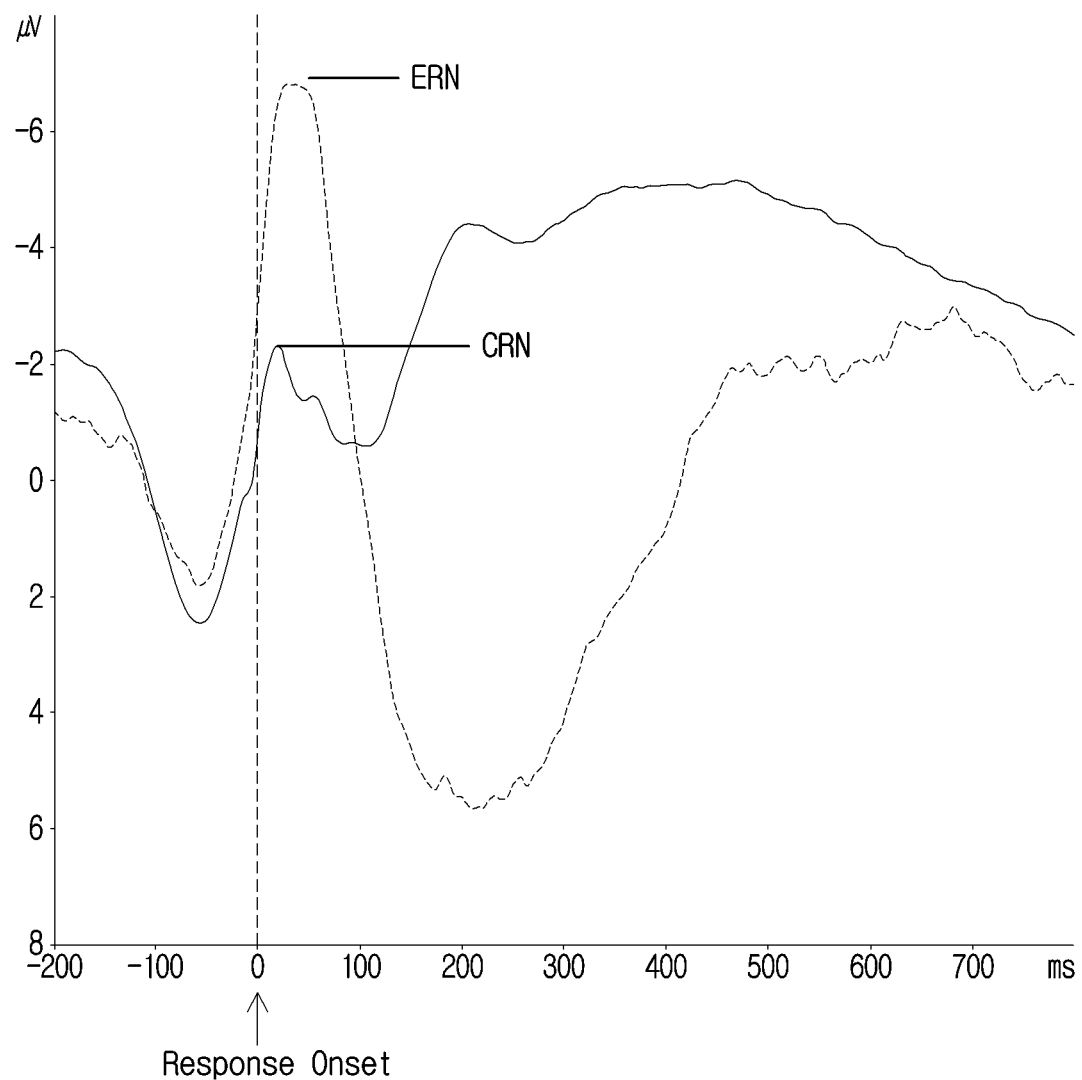
FIG. 5 is a view illustrating general waveforms of ERN and CRN according to one form of the present disclosure.

For yet another example, CRN (Correct-Related Negativity) is an ERP generated by a correct trial and is a negative value that is smaller than ERN. Like ERN, CRN may be generated in the initial latent period (for example, 0~100 ms). FIG. 5 is a view illustrating general waveforms of ERN and CRN in one form of the present disclosure.

For yet another example, Pc (Correct Positivity) is an event-related potential generated following CRN. It is an event-related potential generated in about 150~300 ms after the onset of correct response. The relation between CRN and Pc may be similar to the relation between ERN and Pe.

Meanwhile, ERPs may be classified into stimulus-locked ERPs and response-locked ERPs. The stimulus-locked ERPs and the response-locked ERPs may be divided according to criteria like evoking cause of ERP and response time. For example, an ERP evoked from a moment when a word or a picture is presented to a user from outside may be called a stimulus-locked ERP. In addition, for example, an ERP evoked from a moment when a user speaks or pushed a button may be called a response-locked ERP. Accordingly, based on the above-described criterion, in general, stimulus-locked ERPs are N100, N200, P2, P3, etc., and response-locked ERPs are ERN, Pe, CRN, Pc, FRN, etc.

Meanwhile, brain waves may be classified according to manifesting motives. Brain waves may be classified into spontaneous brain waves (spontaneous potentials) manifested by a user's will and evoked brain waves (evoked potentials) that are naturally manifested according to external stimuli irrespective of the user's will. Spontaneous brain waves may be manifested when a user moves on his/her own or imagines a movement, while evoked brain waves may be manifested by visual, auditory, olfactory and tactile stimuli, for example.

Meanwhile, brain wave signals may be measured in accordance with the International 10-20 system. The International 10-20 system determines measurement points of brain wave signals on the basis of the relationship between the location of an electrode and the cerebral cortex areas.

Figure 6:
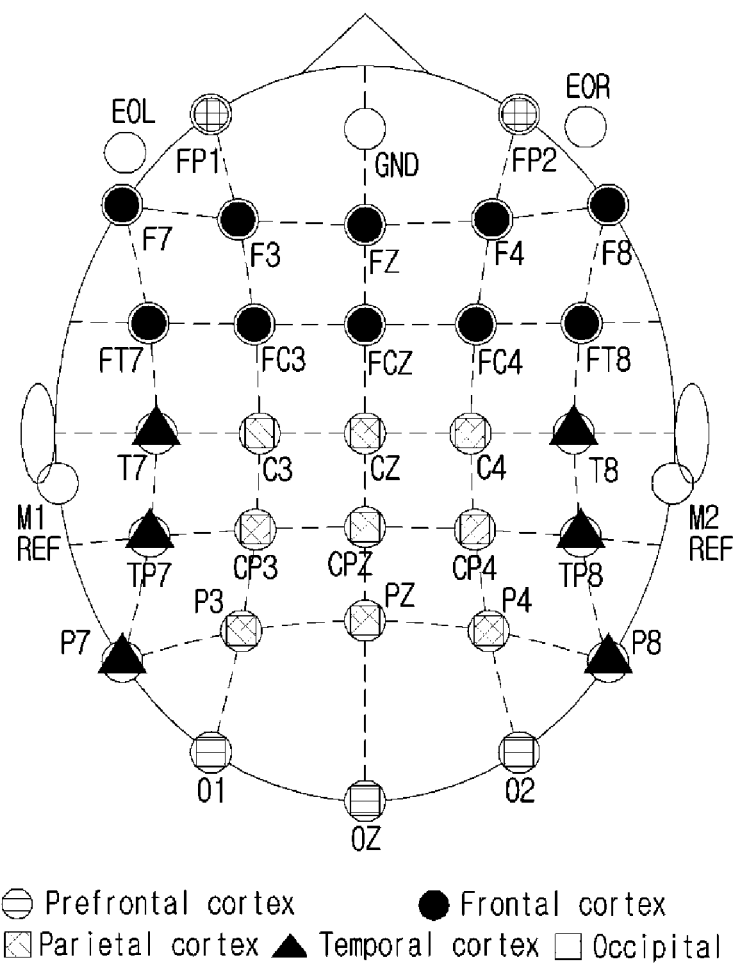
FIG. 6 is a view illustrating EEG measurement channels corresponding to cerebral cortex areas in one form of the present disclosure.

FIG. 6 is a view illustrating EEG measurement channels corresponding to the cerebral cortex areas according to one form of the present disclosure.

Referring to FIG. 6, brain areas (Prefrontal cortex FP1, FP2; Frontal cortex F3, F4, F7, F8, FZ, FC3, FC4, FT7, FT8, FCZ; Parietal cortex C3, C4, CZ, CP3, CP4, CPZ, P3, P4, PZ; Temporal cortex T7, T8, TP7, TP8, P7, P8; Occipital cortex O1, O2, OZ) correspond to 32 brain wave measurement channels. For each of the channels, data may be obtained and analysis may be performed for each cerebral cortex area by using the data.

Figure 7:
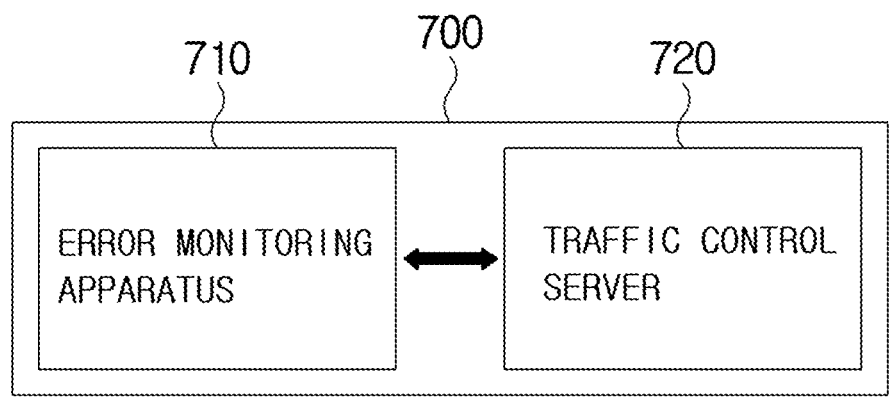
FIG. 7 is a block diagram illustrating a configuration of a traffic surveillance system using error monitoring in one form of the present disclosure.

FIG. 7 is a block diagram illustrating a configuration of a traffic surveillance system using error monitoring in some forms of the present disclosure.

In some forms of the present disclosure, a response-locked ERP is generated when a mistake or error is recognized. In addition, the response-locked ERP may be generated not only as a response to his/her own mistake or error but also as a response to a mistake or error of others. At this time, the response-locked ERP may include ERN, Pe, CRN, Pc, FRN, etc.

Meanwhile, violation of traffic rules may be determined as a kind of mistake or error. Accordingly, by analyzing a brain wave signal of an observer who observes a mobility violating traffic rules, it is possible to acquire a response-locked ERP generated when a mistake or error is recognized. Meanwhile, the mobility may include a vehicle, a mobile/transport apparatus, etc.

Therefore, the traffic surveillance system of the present disclosure may detect a traffic rule violation mobility by using the response-locked ERP obtained from an observer who observes the mobility violating traffic rules. In addition, the traffic surveillance system may impose sanctions such as a fine, a penalty, a forfeit, etc. on the detected mobility.

Referring to FIG. 7, the traffic surveillance system 700 may include an error monitoring apparatus 710 and/or a traffic control server 720. It should be noted, however, that only some of the components necessary for explaining some forms of the present disclosure are shown, and the components included in the traffic surveillance system 700 are not limited to the above-described example. For example, two or more constituent units may be implemented in one constituent unit, and an operation performed in one constituent unit may be divided and executed in two or more constituent units. Also, some of the constituent units may be omitted or additional constituent units may be added.

The error monitoring apparatus 710 in some forms of the present disclosuremay transmit error information of a mobility to a server.

For example, the error monitoring apparatus 710 may collect the ERP for at least one passenger in a first mobility for a predetermined time. In addition, the error monitoring apparatus 710 may analyze the ERP collected during the predetermined time. In addition, the error monitoring apparatus 710 may transmit error information of the first mobility to the traffic control server 720 based on the result of analysis.

Herein, the first mobility may mean a mobility in which an observer who observes a mobility violating traffic rules rides.

At this time, the error information of the first mobility may include information on a time when an ERP for at least one passenger in the first mobility is generated, position information of the first mobility and/or operation information of a second mobility. Herein, the second mobility is different from the first mobility and may refer to a mobility causing the ERP. That is, the second mobility may mean a mobility which violates predetermined traffic rules.

Figure 9:
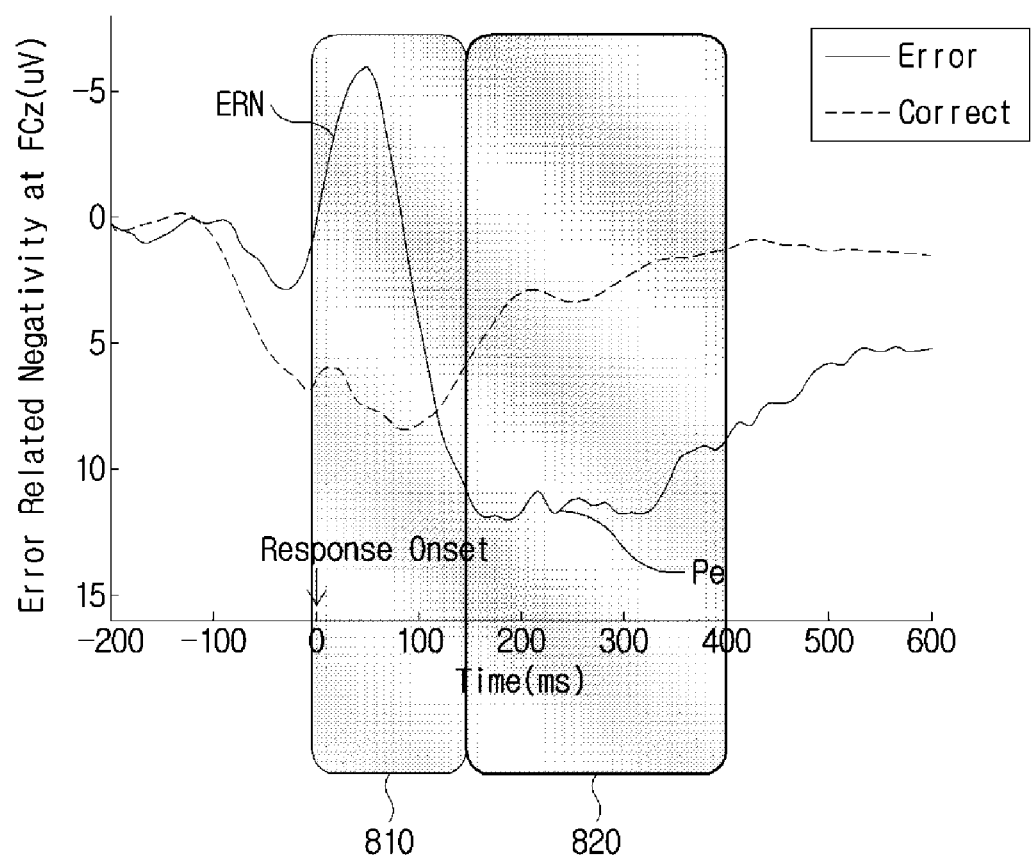
FIG. 9 is a view illustrating a measurement time range, when target ERPs are ERN and Pe, in one form of the present disclosure.
Figure 10:
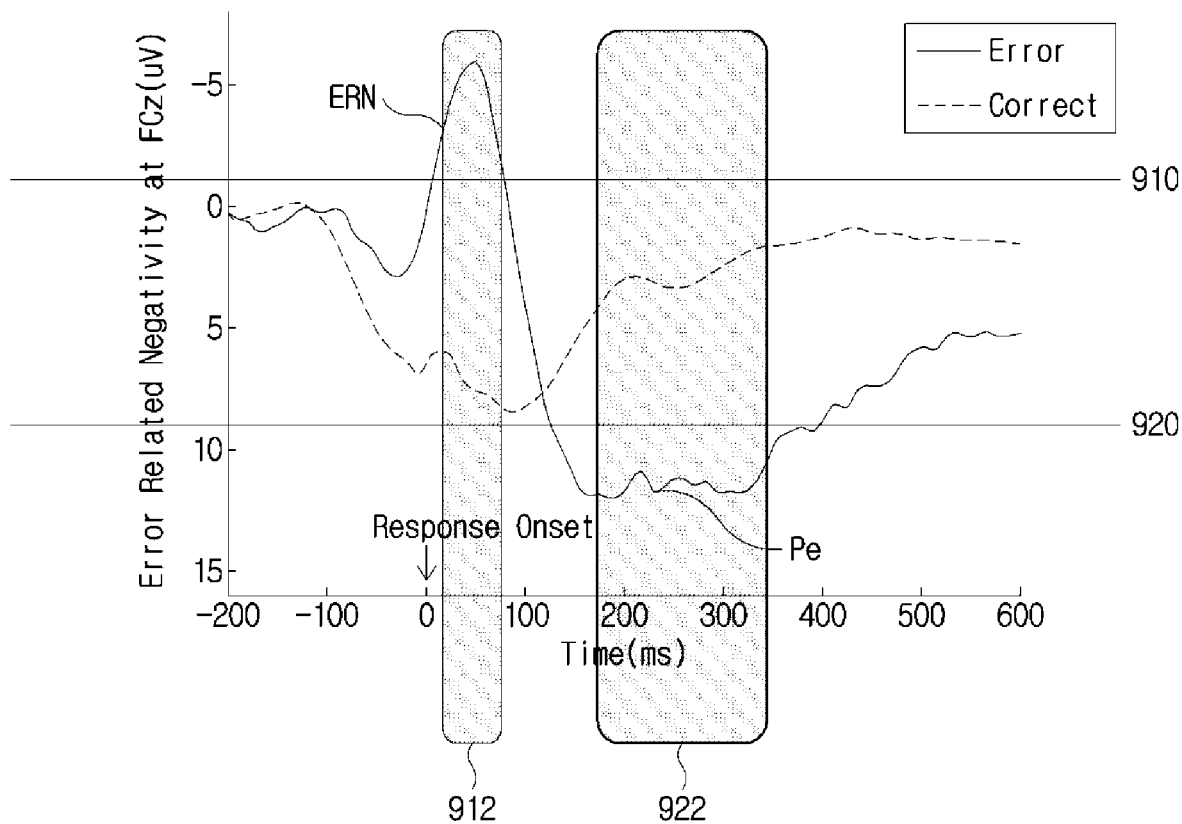
FIG. 10 is a view illustrating a process of comparing a target ERP with a predetermined threshold, when target ERPs are ERN and Pe respectively, in one form of the present disclosure.

More detailed operation of the error monitoring apparatus 710 will be described below with reference to FIGS. 8 to 10.

In addition, the traffic control server 720 in some forms of the present disclosuremay determine a traffic rule violation mobility using the error information of the mobility received from the error monitoring apparatus 710. Herein, the traffic control server may mean a server capable of collecting and analyzing data provided by the mobility and determining whether to violate traffic rules and may mean, for example, a traffic condition control server of a district police station.

For example, the traffic control server 720 may receive the error information of the first mobility from the error monitoring apparatus 710. In addition, the traffic control server 720 may determine a second mobility based on the error information of the first mobility.

More detailed operation of the traffic control server 720 will be described below with reference to FIG. 11.

Figure 8:
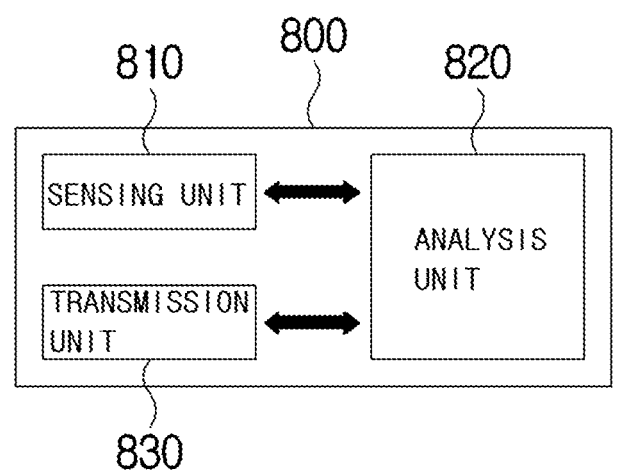
FIG. 8 is a block diagram illustrating a configuration of an error monitoring apparatus in one form of the present disclosure.

FIG. 8 is a block diagram illustrating a configuration of an error monitoring apparatus in some forms of the present disclosure.

Referring to FIG. 8, an error monitoring apparatus 800 may include a sensing unit 810, an analysis unit 820 and/or a transmission unit 830. It should be noted, however, that only some of the components necessary for explaining some forms of the present disclosure are shown, and the components included in the error monitoring apparatus 800 are not limited to the above-described example. For example, two or more constituent units may be implemented in one constituent unit, and an operation performed in one constituent unit may be divided and executed in two or more constituent units. Also, some of the constituent units may be omitted or additional constituent units may be added.

Meanwhile, the error monitoring apparatus 800 of FIG. 8 may be a form of the error monitoring apparatus 710 of FIG. 7.

The error monitoring apparatus 800 in some forms of the present disclosure may collect ERP for at least one passenger in a mobility for a predetermined time. In addition, the sensing unit 810 may perform the above-described operation.

Herein, the ERP may mean a response-locked ERP. In addition, the response-locked ERP may include ERN, Pe, CRN, Pc and FRN. In addition, apart from the ERN, Pe, CRN, Pc and FRN, other ERPs obtained after a response occurs (that is, response onset) may be included. In addition, the response-locked ERP may include a plurality of ERPs.

In addition, herein, collecting the ERP for a predetermined time may include a process of measuring a brain wave signal of at least one passenger in a mobility and detecting an ERP from the measured brain wave signal.

In FIGS. 1 to 6, as described above, ERN, Pe, CRN, Pc and/or FRN may be generated as responses to wrong behaviors like an error or a mistake or responses to right behaviors. Accordingly, if the ERP is used, it is possible to determine whether or not a corresponding passenger has performed a wrong behavior. Also, based on the determination, a mobility may be controlled to suit a purpose.

For example, when a driver has to make a right turn but makes a left turn or when a driver has to make a left turn but continues straight, ERN and/or Pe may be generated.

For another example, while driving according to a guide of a navigation system, if a driver fails to perform a movement according to the guide, ERN and/or Pe may be generated.

For yet another example, when a driver is in traffic, takes a course for the first time or undergoes a tense and stressful situation on road, ERN and/or Pe may be generated.

In addition, the predetermined time may mean about 0 to 400 ms after the onset of a specific response. In addition, the predetermined time may include a time range where the above-described response-locked ERP may be obtained. In addition, the predetermined time may vary according to the type of a response-locked ERP and may have a plurality of time ranges. For example, a first time range may be given to obtain a first ERP, and a second time range may be given to obtain a second ERP.

For example, when a first ERP is ERN and a second ERP is Pe, a first time range may be about 0 to 150 ms that is the main measurement section of ERN, and a second time range may be about 150 to 400 ms that is the main measurement section of Pe. FIG. 9 is a view illustrating a measurement time range, when target ERPs are ERN and Pe, in some forms of the present disclosure. Referring to FIG. 8, ERN may be obtained in a first time range 910, and Pe may be obtained in a second time range 920.

For another example, when a first ERP is ERN and a second ERP is CRN, a first time range may be about 0 to 200 ms that is the main measurement section of ERN, and a second time range may be about 0 to 200 ms that is the main measurement section of CRN.

In addition, the passenger may include not only the driver in a mobility but also another passenger.

In addition, the error monitoring apparatus 800 of the present disclosure may analyze the ERP collected for the predetermined time. In addition, the analysis unit 820 may perform the above-described operation.

Herein, the analysis may include a process of comparing the amplitude of the ERP, which is collected for the predetermined time, with a predetermined threshold.

Meanwhile, the threshold may be a preset value or a value input by a user. In addition, the threshold may have a different amplitude for each passenger from whom an ERP is collected. For example, it may be a value reflecting the brain wave signal characteristic of each passenger. In order to reflect the analysis result of the brain wave signal characteristic, a predetermined learning process may be performed in advance for response-locked ERP characteristics displayed in a passenger's brain wave signal. In addition, the threshold may vary according to the type of ERP and may have a plurality of thresholds. FIG. 10 is a view illustrating a process of comparing a target ERP with a predetermined threshold, when target ERPs are ERN and Pe respectively, in some forms of the present disclosure. Referring to FIG. 10, in the case of ERN, the amplitude thereof may be compared with a first threshold 1010. In the case of Pe, the amplitude thereof may be compared with a second threshold 1020.

In addition, the analysis may include a process of determining whether or not the amplitude of the ERP is equal to or greater than a predetermined threshold (that is, out of a predetermined threshold range) during a predetermined time interval. Referring to FIG. 10, in the case of ERN, the amplitude of ERN may be compared with a first threshold 1010 to determine whether or not the amplitude of ERN is equal to or greater than the first threshold 1010 during a third time range 1012. In the case of Pe, the amplitude of Pe may be compared with a second threshold 1020 to determine whether or not the amplitude of Pe is equal to or smaller than the second threshold 1020 during a fourth time range 1022.

In addition, the analysis may be performed by using a brain wave signal template of each passenger. Herein, a brain wave signal template may mean a brain wave signal in a time domain, which is previously obtained within a predetermined time range after a response onset for an arbitrary movement. The response may include an error, a mistake, a correct response and the like. The previously-made brain wave signal template may be scaled in the analysis process. In other words, the amplitude of a brain wave signal graph may be increased or decreased at a predetermined rate. For example, the analysis may be performed by comparing an amplitude-time graph waveform of a single ERP and/or a plurality of ERPs obtained for a predetermined time with the predetermined brain wave signal template.

Meanwhile, the analysis may be preceded by a process of cognizing generation of an ERP by using a time when the characteristic of a brain wave signal appears and/or using the pattern of a brain wave signal. In addition, the analysis may include a processing of extracting an ERP.

In addition, an ERP used for the analysis may be a statistical value of the ERP collected for a predetermined time. For example, the statistical value may mean an average value, a weighted average value, a maximum value and a minimum value.

In addition, the error monitoring apparatus 800 of the present disclosure may transmit the error information of the first mobility to the traffic control server based on the result of analysis in the analysis unit 820. In addition, the transmission unit 830 may perform the above-described operation.

Herein, the error information of the first mobility may include information on a time when the ERP is generated, the waveform of the ERP, the position information of the first mobility and/or operation information of the second mobility.

At this time, the ERP may mean an ERP for at least one passenger in the first mobility.

The information on the time when the ERP is generated may mean a response onset time of the ERP. That is, referring to FIG. 10, this may mean a response onset time. For example, when the ERP is ERN, since the main measurement section of the ERN is about 0 to 150 ms after a response occurrence time, a time obtained by subtracting about 0 to 150 ms from the measurement time of ERN may be the information on the time when the ERP is generated.

Alternatively, the information on the time when the ERP is generated may mean the measurement time of the ERP.

In addition, the position information of the first mobility may mean the position of the first mobility when the ERP is measured. Meanwhile, the position of the first mobility may be obtained using various types of position recognition systems including a global positioning system (GPS) or using the movement direction or effective speed of the first mobility, road slope information, etc.

In addition, the operation information of the second mobility may mean operation of the second mobility which has caused the ERP. For example, the operation information may include traffic rule violation such as the second mobility information driving over a centerline, speeding or violation of traffic sign.

Meanwhile, the operation information of the second mobility may be obtained from an image acquisition apparatus such as a camera included in the first mobility.

Meanwhile, the operation information of the second mobility may be obtained by analyzing the ERP as described above.

For example, the ERP and the operation information of the second mobility related thereto may have a mapping relationship with each other. For example, depending on the amplitude (size) or waveform of an obtained ERP, the operation information of the second mobility may be mapped as shown in the example of Table 1.

TABLE 1

| Event-related potential (ERP) | Amplitude of event | Specific event |
|---|---|---|
| ERP > First threshold | Large | First event |
| First threshold ≥ ERP & ERP ≥ Second threshold | Middle | Second event |
| ERP < Second threshold | Small | Third event |

Referring to Table 1, an event-related potential is ERP, and the amplitude of an event may mean the seriousness of an event taking place. Operation of the second mobility may be classified into a first event, a second event and a third event according to each step, and the classification may vary according to passengers. In addition, the same event may be included in multiple steps.

Specifically, when the ERP is greater than the first threshold, the predetermined event may be mapped to the first event. In addition, when the ERP is less than the second threshold, the predetermined event may be mapped to the third event. In addition, when the predetermined event is not the first event and the third event, the predetermined event may be mapped to the second event.

For example, a first event has high seriousness and may include 10 gross negligence cases of traffic rules, such as driving over centerline and violation of traffic sign. The 10 gross negligence cases of traffic rules may be shown in Table 2.

TABLE 2

| No | 10 Gross Negligence Events | Details |
|---|---|---|
| 1 | Violation of traffic sign or instruction | ⓐ A case of violating a signal or instruction given by a police officer (including an exemplary driver and an MP (Military Police)) directing traffic. ⓑ A case of not following but violating a traffic signal ⓒ In the case of causing an accident by obstructing the way of other vehicles in a zone with PPLT (Protected/Permitted Left-Turn) sign, the responsibility for traffic sign violation cannot be avoided. |
| 2 | Driving over centerline | ⓐ Driving over centerline and crossing, making U-turn and driving backward on the highways (expressways). ⓑ Even if only a part of a vehicle slightly steps on or crosses the centerline, it is equivalent to driving over centerline. ⓒ In the case of crossing over the centerline in an irresistible or unavoidable situation like collision or icy road, it is not considered as driving over centerline. ⓓ Private centerlines installed by residents in apartment complexes or residential areas are not centerlines. |
| 3 | Overspeed exceeding 20 km/h | ⓐ An accident taken place while driving at a speed exceeding the speed limit of 20 km/h |
| 4 | Violation of overtaking and method thereof | An accident taken place while overtaking ⓐ in case another vehicle is driven in the left lane alongside the vehicle ahead, ⓑ in case the vehicle ahead is overtaking another vehicle, or overtaking in an intersection, a ramp or a tunnel. ⓒ Overtaking prohibited areas: Intersection, bend, top of hill, downhill, bridge, tunnel, and other places with probation sign ⓓ Prohibited cases of overtaking: vehicles ahead advancing side by side, following the vehicle ahead overtaking another vehicle, other cases prohibited by laws |
| 5 | Railroad crossing violation | ⓐ At railroad crossing, it is necessary to stop first and then safely cross. |
| 6 | Violation related to crosswalk | ⓐ Accident at a crosswalk with traffic lights- Applicable only when the stop signal for vehicles and the walk signal are on. ⓑ Accident at a crosswalk without traffic light- Applicable only within the crosswalk mark ⓒ If a victim of an accident was riding a bicycle or a motorcycle, he/she cannot be protected as a pedestrian. |

TABLE 2-continued

| No | 10 Gross Negligence Events | Details |
|---|---|---|
| 7 | Driving without license | ⓐ A case of driving a vehicle without license |
|   |   | ⓑ A case of driving a vehicle during the revocation or suspension period of license |
|   |   | ⓒ A case of driving a vehicle that the driver's license does not cover |
|   |   | ⓓ Along with criminal responsibility, even if a driver is insured, he/she cannot receive insurance. |
|   |   | ⓔ In case the license is returned due to excessive penalty points but the administrative measure has not been taken, the accident is not categorized under driving without license. |
| 8 | Drunk driving | ⓐ In case the level of alcohol exceeds 0.5 ml in 1 ml of blood |
|   |   | ⓑ In case 0.25 ml or higher level of alcohol is detected in 1 l of breath |
|   |   | ⓒ In case the breath alcohol level (BAL) is 0.05%, drunk driving is conducted. |
| 9 | Sidewalk trespassing | ⓐ A case of trespassing a sidewalk or driving in violation of a method of crossing a sidewalk |
| 10 | Starting with a door open | ⓐ A case of driving in violation of the passenger fall prevention duty → A case of pulling over or staring with a door open |

Figure 11:
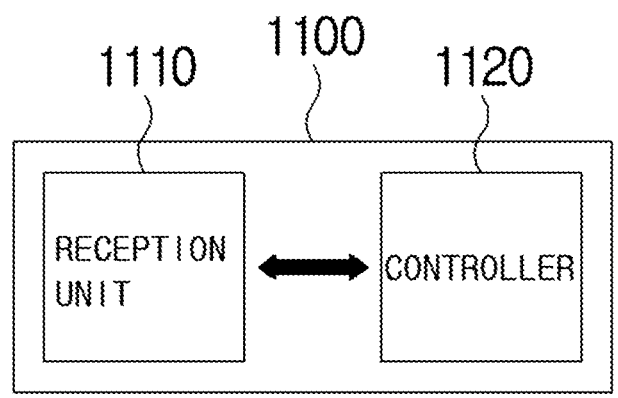
FIG. 11 is a block diagram illustrating a configuration of a traffic control server in one form of the present disclosure.

FIG. 11 is a block diagram illustrating a configuration of a traffic control server in some forms of the present disclosure.

Referring to FIG. 11, the traffic control server 1100 may include a reception unit 1110 and/or a controller 1120. It should be noted, however, that only some of the components necessary for explaining some forms of the present disclosure are shown, and the components included in the traffic control server 1100 are not limited to the above-described example. For example, two or more constituent units may be implemented in one constituent unit, and an operation performed in one constituent unit may be divided and executed in two or more constituent units. Also, some of the constituent units may be omitted or additional constituent units may be added.

Meanwhile, the traffic control server 1100 of FIG. 11 may be a form of the traffic control server 720 of FIG. 7.

The traffic control server 1100 in some forms of the present disclosuremay receive the error information of the first mobility from the first mobility. In addition, the reception unit 1110 may perform the above-described operation.

In addition, the traffic control server 1100 in some forms of the present disclosure may determine a second mobility based on the error information of the first mobility. Alternatively, the traffic control server 1100 in some forms of the present disclosure may determine whether the second mobility violates predetermined traffic rules based on the error information of the first mobility.

In addition, the traffic control server 1100 in some forms of the present disclosure may impose, on the second mobility, a fine, a penalty or a forfeit corresponding to the violation of the predetermined traffic rules, upon determining that the second mobility has violated the predetermined traffic rules. In addition, the controller 1120 may perform the above-described operation.

For example, the traffic rules may mean one of 10 gross negligence cases of traffic rules as shown in the example of Table 2.

Meanwhile, the traffic surveillance system may determine that the second mobility has violated traffic rules at this time with a higher probability, when the peak value in the waveform information of the ERP obtained from the first mobility is large.

Meanwhile, the traffic surveillance system may obtain a result with higher reliability, by using the error information of a plurality of mobilities.

For example, when there is little difference between timings of generation of the ERPs obtained from the plurality of mobilities, the traffic surveillance system may determine that the second mobility has violated traffic rules at this time with higher probability.

As another example, when the waveforms of the ERPs obtained from the plurality of mobilities are similar, the traffic surveillance system may determine that the second mobility has violated traffic rules at this time with higher probability.

Accordingly, the traffic control server 1100 in some forms of the present disclosure may further receive error information of a third mobility from the third mobility. In addition, the reception unit 1110 may perform the above-described operation.

Herein, the third mobility is different from the first mobility and the second mobility and may mean a mobility in a predetermined range from the first mobility. Alternatively, the third mobility may mean a mobility within a predetermined range from the second mobility.

In addition, the predetermined range may mean a certain range from a reference mobility, such as a few meters in radius and a few meters in the rear.

Meanwhile, the traffic control server 1100 in some forms of the present disclosure may further receive the error information of a third party from the third party. In addition, the reception unit 1110 may perform the above-described operation. Herein, the third party may mean a person who observes the second mobility violating traffic rules without riding in the mobilities such as the first to third mobilities.

In addition, the traffic control server 1100 in some forms of the present disclosure may determine the second mobility based on the error information of the first mobility and the error information of the third mobility. In addition, the controller 1120 may perform the above-described operation.

For example, the statistical value of the error information of the first mobility and the error information of the third mobility may be used. For example, the statistical value may mean an average value, a weighted average value, a maximum value and a minimum value.

Figure 12:
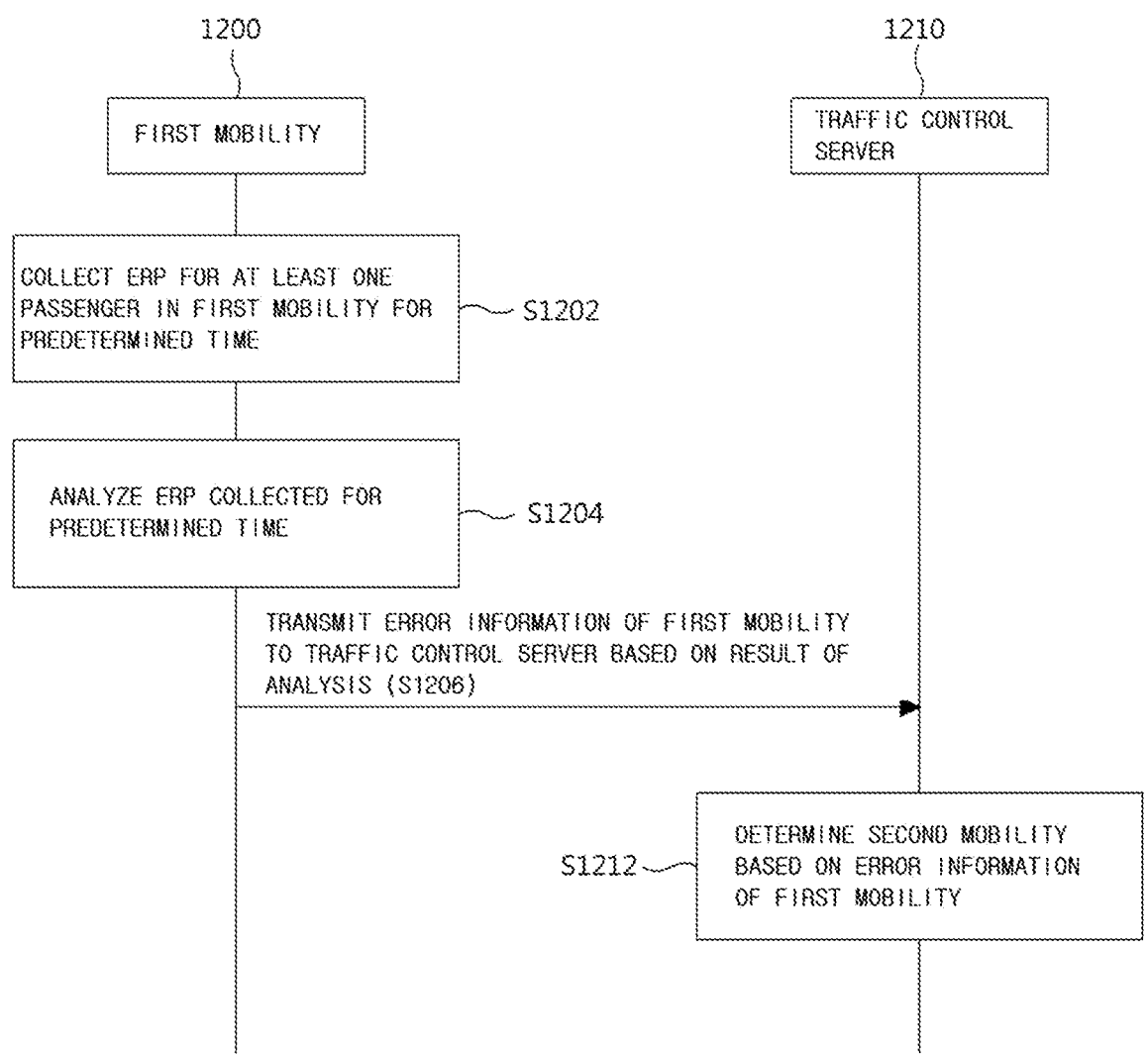
FIG. 12 is a flowchart illustrating a method of operating a traffic surveillance system using error monitoring in one form of the present disclosure.

FIG. 12 is a flowchart illustrating a method of operating a traffic surveillance system using error monitoring in some forms of the present disclosure.

The traffic surveillance system in some forms of the present disclosure may include an error monitoring apparatus 1200 for transmitting error information of a mobility to a server and/or a traffic control server 1210 for determining a traffic rule violation mobility using the error information of the mobility.

Referring to FIG. 12, the error monitoring apparatus 1200 may collect an ERP for at least one passenger in a mobility for a predetermined time (S1202).

In addition, the error monitoring apparatus 1200 may analyze the ERP collected for the predetermined time (S1204).

Herein, the ERP may include at least one of ERN (Error-Related Negativity) and Pe (Error Positivity). In addition, the ERP may further include at least one of CRN (Correct-Related Negativity) and Pc (Correct Positivity).

Herein, collecting the ERP for a predetermined time may include a process of measuring a brain wave signal of at least one passenger in a mobility and detecting an ERP from the measured brain wave signal.

In addition, the error monitoring apparatus 1200 may transmit the error information of a first mobility to the traffic control server 1210 based on the result of analysis in step S1204 (S1206).

Herein, the analysis may mean comparing the amplitude of the ERP, which is collected for the predetermined time, with a predetermined threshold. In addition, the analysis may mean determining whether or not the amplitude of the ERP is within a predetermined threshold range during a predetermined time interval.

Meanwhile, the analysis may be preceded by a process of cognizing generation of an ERP by using a time when the characteristic of a brain wave signal appears and/or using the pattern of a brain wave signal. In addition, the analysis may include a processing of extracting an ERP.

At this time, the predetermined threshold may be differently determined according to at least one of the type of the ERP and the passenger from whom the ERP is obtained.

In addition, the error information of the first mobility may include information on a time when an ERP for at least one passenger in the first mobility is generated, the waveform of the ERP, position information of the first mobility and/or operation information of a second mobility.

At this time, the second mobility is different from the first mobility and may refer to a mobility causing the ERP.

Meanwhile, the traffic control server 1210 may receive the error information of the first mobility from the error monitoring apparatus 1200 (S1206).

In addition, the traffic control server 1210 may determine the second mobility based on the error information of the first mobility (S1212). Alternatively, the traffic control server 1210 may determine whether the second mobility has violated predetermined traffic rules based on the error information of the first mobility.

Figure 13:
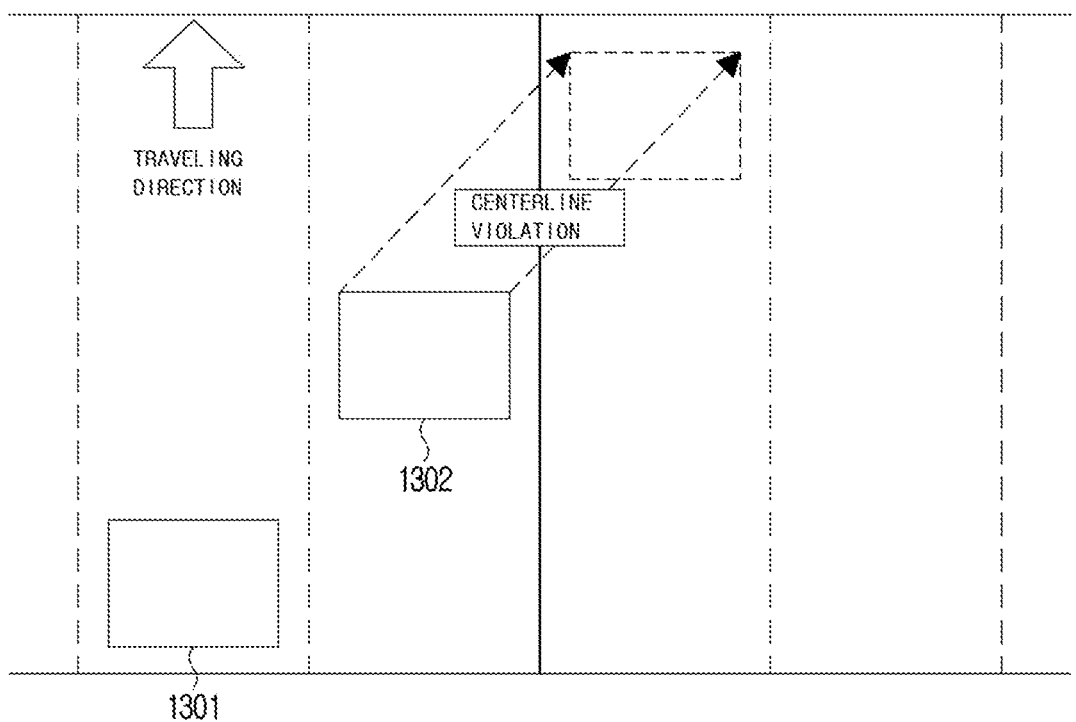
FIG. 13 is a view illustrating operation of a first mobility in which an observer who has observed a second mobility driving over a centerline while traveling, in a traffic surveillance system in one form of the present disclosure.

FIG. 13 is a view illustrating operation of a first mobility in which an observer who has observed a second mobility driving over a centerline while traveling, in a traffic surveillance system in some forms of the present disclosure.

Referring to FIG. 13, it is assumed that a second mobility 1302, which is traveling ahead of a first mobility 1301 in the same direction as the traveling direction of the first mobility 1301, drives over a centerline (hereinafter referred to as "centerline violation event").

The error monitoring apparatus in some forms of the present disclosure may collect the ERP from at least one passenger in the first mobility 1301 for the predetermined time. The ERP may be continuously, for example, periodically measured and stored before occurrence of the centerline violation event. The error monitoring apparatus may store the display time of the ERP, the position information of the first mobility 1301, etc. In addition, the error monitoring apparatus may also store the waveform of the ERP, the operation information of the second mobility 1302, etc.

The error monitoring apparatus in some forms of the present disclosure may transmit the collected and stored information to the traffic control server. For example, the traffic control server may be a traffic condition control server of a district police station.

The traffic control server in some forms of the present disclosure may determine the second mobility 1302, which has driven over the centerline, using the information received from the error monitoring apparatus. Meanwhile, the traffic control server may specify a position where the centerline violation event has occurred based on the received information. In addition, the mobility which has driven over the centerline may be determined, by examining the display time of the ERP from a closed-circuit television (CCTV) located in a predetermined range from the corresponding position.

The traffic control server in some forms of the present disclosure may impose, on the determined mobility, a fine, a penalty or a forfeit corresponding to centerline violation.

Meanwhile, the traffic surveillance system may use ERP information of a plurality of mobilities or a plurality of observers to ensure reliability.

For example, when there is little difference between timings of generation of the ERPs obtained from the plurality of observers or the plurality of mobilities around the corresponding position, the traffic surveillance system may determine that the second mobility 1302 has violated traffic rules at this time with higher probability.

As another example, when the waveforms of the ERPs obtained from the plurality of observers or the plurality of mobilities around the corresponding position are similar, the traffic surveillance system may determine that the second mobility 1302 has violated traffic rules at this time with higher probability.

As another example, when the waveforms of the ERPs obtained from the plurality of observers or the plurality of mobilities around the corresponding position are different, the traffic surveillance system may determine that the second mobility 1302 does not violate traffic rules.

As another example, when the waveforms of the ERPs obtained from the plurality of observers or the plurality of mobilities around the corresponding position are different, the traffic surveillance system may determine that the existing traffic rules are not suitable for traffic conditions at the corresponding position and reconfigure the traffic rules to be suitable for the corresponding position.

Meanwhile, the traveling direction of the second mobility 1302 may not be equal to that of the first mobility 1301. In addition, the second mobility 1302 may not travel ahead of the first mobility 1301. Various conditions in which a passenger in the first mobility 1301 may observe centerline violation of the second mobility 1302 regardless of the traveling direction or the traveling speed may be included.

According to the present disclosure, it is possible to provide a traffic surveillance system.

In addition, according to the present disclosure, it is possible to provide a traffic surveillance system for determining whether to follow traffic rules based on error monitoring.

In addition, according to the present disclosure, it is possible to provide an error monitoring apparatus and method for performing error monitoring.

In addition, according to the present disclosure, it is possible to provide a traffic control server for determining whether to follow traffic rules of a mobility based on error monitoring, and a method of operating the same.

Effects obtained in the present disclosure are not limited to the above-mentioned effects, and other effects not mentioned above may be clearly understood by those skilled in the art from the following description.

Although exemplary methods of the present disclosure are described as a series of operation steps for clarity of a description, the present disclosure is not limited to the sequence or order of the operation steps described above. The operation steps may be simultaneously performed, or may be performed sequentially but in different order. In order to implement the method of the present disclosure, additional operation steps may be added and/or existing operation steps may be eliminated or substituted.

Various forms of the present disclosure are not presented to describe all of available combinations but are presented to describe only representative combinations. Steps or elements in various forms may be separately used or may be used in combination.

In addition, various forms of the present disclosure may be embodied in the form of hardware, firmware, software, or a combination thereof. When the present disclosure is embodied in a hardware component, it may be, for example, an application specific integrated circuit (ASIC), a digital signal processor (DSP), a digital signal processing device (DSPD), a programmable logic device (PLD), a field programmable gate array (FPGA), a general processor, a controller, a microcontroller, a microprocessor, etc.

The scope of the present disclosure includes software or machine-executable instructions (for example, operating systems (OS), applications, firmware, programs) that enable methods of various forms to be executed in an apparatus or on a computer, and a non-transitory computer-readable medium storing such software or machine-executable instructions so that the software or instructions can be executed in an apparatus or on a computer.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. An error monitoring apparatus comprising:
    a sensor configured to collect an Event-Related Potential (ERP) for at least one passenger in a first mobility for a predetermined amount of time, wherein the ERP comprises a first ERP and a second ERP;
    an analyzer configured to analyze the first ERP collected for a first predetermined amount of time of the predetermined amount of time and the second ERP collected for a second predetermined amount of time of the predetermined amount of time, wherein the first and second predetermined amount are determined based on each type of the ERP; and
    a transmitter configured to transmit error information of the first mobility to a traffic control server based on a result of analysis of the ERP,
    wherein the error information of the first mobility includes at least one of information on a time when the ERP is generated, a waveform of the ERP, position information of the first mobility, and operation information of a second mobility obtained by a camera included in the first mobility,
    wherein the second mobility is different from the first mobility and has caused the ERP; and
    wherein the traffic control server determines whether the second mobility violates a traffic rule violation of predetermined traffic rules based on the error information.

2. The error monitoring apparatus of claim 1, wherein the second predetermined amount of time is different from the first predetermined amount of time in case of the first ERP is Error-Related Negativity (ERN) and the second ERP is Error Positivity (Pe), and
    wherein the second predetermined amount of time is equal to the first predetermined amount of time in case of the first ERP is Error-Related Negativity (ERN) and the second ERP is Correct-Related Negativity (CRN).

3. The error monitoring apparatus of claim 1, wherein the analyzer is configured to compare an amplitude of the collected ERP with a predetermined threshold.

4. The error monitoring apparatus of claim 1, wherein the analyzer is configured to determine a predetermined threshold based on at least one of a type of the ERP or the at least one passenger.

5. The error monitoring apparatus of claim 4, wherein the transmitter is configured to:
    transmit the error information of the first mobility to the traffic control server, when the amplitude of the collected ERP is out of a predetermined threshold range.

6. The error monitoring apparatus of claim 1, wherein the sensor is configured to: measure a brain wave signal of the at least one passenger in the first mobility;
    and detect the ERP from the measured brain wave signal, wherein the ERP includes a response-locked ERP.

7. The error monitoring apparatus of claim 1, wherein the analyzer is configured to: analyze the collected ERP using a brain wave signal template of the at least one passenger, wherein the brain wave signal is a brain wave signal in a time domain that is previously obtained within a predetermined time range after generation of the ERP.

8. A traffic control server comprising:
    a receiver configured to receive error information of a first mobility generated by an error monitoring apparatus of the first mobility; and
    a controller configured to determine whether a second mobility violates a traffic rule violation of predetermined traffic rules based on the error information of the first mobility, wherein the error information of the first mobility includes at least one of information on a time when the ERP is generated, a waveform of the ERP, position information of the first mobility, and operation information of a second mobility obtained by a camera included in the first mobility,
    wherein the second mobility is different from the first mobility and has caused the ERP,
    wherein the error monitoring apparatus comprises a sensor to collect an Event-Related Potential (ERP) for at least one passenger in the first mobility for a predetermined amount of time and an analysis unit analyzes the collected ERP to generate the error information;

wherein the ERP comprises a first ERP and a second ERP; and the first ERP is collected for a first predetermined amount of time of the predetermined amount of time and the second ERP is collected for a second predetermined amount of time of the predetermined amount of time, and wherein the first and second predetermined amount of time are determined based on each type of ERP.

9. The traffic control server of claim 8, wherein the controller is configured to: impose, on the second mobility, at least one of a fine, a penalty or a forfeit corresponding to the traffic rule violation of the predetermined traffic rules when the controller determines that the second mobility has violated the traffic rulers violation.

10. The traffic control server of claim 8, wherein: the receiver is further configured to receive error information of a third mobility from the third mobility, the controller is configured to determine the second mobility violates the traffic rule violation of the predetermined traffic rules based on the error information of the first mobility and the error information of the third mobility, wherein the third mobility is different from the first mobility and the second mobility and is located in a predetermined range from the first mobility.

11. A traffic surveillance system comprising:

an error monitoring apparatus comprises a transmitter to transmit error information of a first mobility to a traffic control server; and a traffic control server configured to determine whether a second mobility has violated a traffic rule violation of predetermined traffic rules using the error information of the first mobility, wherein the error monitoring apparatus is configured to:

collect an Event-Related Potential (ERP) for at least one passenger in the first mobility for a predetermined amount of time;

analyze the ERP collected for the predetermined amount of time to generate the error information; and transmit the error information of the first mobility to the traffic control server based on a result of analysis of the ERP, wherein the traffic control server is configured to receive the error information of the first mobility from the error monitoring apparatus and determine whether the second mobility violates the traffic rule violation of the predetermined traffic rules based on the error information of the first mobility, wherein the error information of the first mobility includes at least one of information on a time when the ERP is generated, a waveform of the ERP, position information of the first mobility and operation information of the second mobility obtained by a camera included in the first mobility, wherein the second mobility is different from the first mobility and has caused the ERP, wherein the ERP comprises a first ERP and a second ERP; and the first ERP is collected for a first predetermined amount of time of the predetermined amount of time and the second ERP is collected for a second predetermined amount of time of the predetermined amount of time, and wherein the first and second predetermined amount of time are determined based on each type of ERP.

12. An error monitoring method comprising:

collecting, by an error monitoring apparatus associated with a first mobility, an Event-Related Potential (ERP) for at least one passenger in the first mobility for a predetermined amount of time, wherein the ERP comprises a first ERP and a second ERP;

analyzing, by the error monitoring apparatus, the first ERP collected for a first predetermined amount of time of the predetermined amount of time and the second ERP collected for a second predetermined amount of time, of the predetermined amount of time wherein the first and second predetermined amount of time are determined based on each type of ERP; and transmitting, by the error monitoring apparatus, error information of the first mobility to a traffic control server based on a result of analysis of the ERP, wherein the error information of the first mobility includes at least one of information on a time when the ERP is generated, a waveform of the ERP, position information of the first mobility and operation information of a second mobility obtained by a camera included in the first mobility, and wherein the second mobility is different from the first mobility and has caused the ERP; and wherein the traffic control server determines whether the second mobility has violated a traffic rule violation of predetermined traffic rules based on the error information from the first mobility.

13. The error monitoring method of claim 12, wherein the second predetermined amount of time is different from the first predetermined amount of time in case of the first ERP is Error-Related Negativity (ERN) and the second ERP is Error Positivity (Pe), and wherein the second predetermined amount of time is equal to the first predetermined amount of time in case of the first ERP is Error-Related Negativity (ERN) and the second ERP is Correct-Related Negativity (CRN).

14. The error monitoring method of claim 13, wherein analyzing, by the error monitoring apparatus, the collected ERP comprises:

comparing an amplitude of the collected ERP with a predetermined threshold.

15. The error monitoring method of claim 12, wherein analyzing, by the error monitoring apparatus, the collected ERP comprises:

determining a predetermined threshold based on at least one of a type of the ERP or the at least one passenger.

16. The error monitoring method of claim 15, wherein transmitting, by the error monitoring apparatus, the error information of the first mobility to the traffic control server comprises:

when the amplitude of the collected ERP is out of a predetermined threshold range, transmitting the error information of the first mobility to the traffic control server.

17. The error monitoring method of claim 12, wherein collecting, by the error monitoring apparatus, the ERP comprises:

measuring a brain wave signal of the at least one passenger in the first mobility and detecting the ERP from the measured brain wave signal, wherein the ERP includes a response-locked ERP.

18. The error monitoring method of claim 12, wherein analyzing, by the error monitoring apparatus, the collected ERP comprises:

determining whether an amplitude of the ERP is in a predetermined threshold range for a predetermined time interval.

19. The error monitoring method of claim 12, wherein analyzing, by the error monitoring apparatus, the collected ERP comprises:

analyzing the collected ERP using a brain wave signal template of the at least one passenger,
wherein the brain wave signal is a brain wave signal in a time domain that is previously obtained within a predetermined time range after generation of the ERP.

* * * * *